US012753451B2

(12) United States Patent
Capoluongo et al.

(10) Patent No.: US 12,753,451 B2
(45) Date of Patent: Oct. 6, 2026

(54) METHOD FOR DETERMINING ACTIVE SARS-CoV-2-INFECTIONS

(71) Applicant: CEINGE BIOTECNOLOGIE AVANZATE FRANCO SALVATORE S.C. A R.L., Naples (IT)

(72) Inventors: Ettore Domenico Capoluongo, Rome (IT); Veronica Ferrucci, Portici (IT); Massimo Zollo, Naples (IT)

(73) Assignee: CEINGE BIOTECNOLOGIE AVANZATE FRANCO SALVATORE S.C. A R.L., Naples (IT)

(*) Notice: Subject to any disclaimer, the term of this patent is extended or adjusted under 35 U.S.C. 154(b) by 527 days.

(21) Appl. No.: 18/258,562

(22) PCT Filed: Dec. 23, 2021

(86) PCT No.: PCT/EP2021/087512

§ 371 (c)(1),
(2) Date: Jun. 21, 2023

(87) PCT Pub. No.: WO2022/136651

PCT Pub. Date: Jun. 30, 2022

(65) Prior Publication Data

US 2023/0383369 A1 Nov. 30, 2023

(30) Foreign Application Priority Data

Dec. 23, 2020 (IT) ........................ 102020000032351

(51) Int. Cl.

| | |
|---|---|
| ***A61K 39/12*** | (2006.01) |
| ***A61K 39/00*** | (2006.01) |
| ***A61K 39/215*** | (2006.01) |
| ***A61P 31/14*** | (2006.01) |
| ***C07K 14/08*** | (2006.01) |
| ***C12Q 1/70*** | (2006.01) |

(52) U.S. Cl.

CPC ....... *C12Q 1/701* (2013.01); *C12Q 2600/158* (2013.01)

(58) Field of Classification Search

CPC ........ A61K 2039/5256; A61K 2039/12; A61K 39/215; A61P 31/14; C07K 16/1002

See application file for complete search history.

(56) References Cited

U.S. PATENT DOCUMENTS

2003/0050470 A1* 3/2003 An ........................ C07H 21/00 435/6.14

FOREIGN PATENT DOCUMENTS

| | | | |
|---|---|---|---|
| CN | 111139315 | * | 5/2020 |
| CN | 111187858 | * | 5/2020 |
| CN | 111187858 A | | 5/2020 |
| CN | 111257559 | * | 6/2020 |
| CN | 112760341 | * | 5/2021 |
| CN | 113444835 | * | 9/2021 |
| WO | 2005042767 A2 | | 5/2005 |

OTHER PUBLICATIONS

Alexandersen S. et al., "Sars-CoV-2 genomic and RNAs in diagnostic samples are not an indicator of active replication", Nature Communications, vol. 11, No. 1 Nov. 27, 2020. Retrieved from the Internet: URL: https://www.nature.come/articles/s41467-020-19883-7.pdf.

Perera R. A.P.M. et al., "Sars-CoV-2 virus culture and subgenomic RNA for respiratory specimens from patients with mild coronavirus disease", Emerging Infectious Diseases, vol. 26, No. 11, Nov. 1, 2020, pp. 2701-2704.

Search Report and Written Opinion of PCT/EP2021/087512 issued May 2, 2022.

Van Kampen J J A et al., "Shedding of infectious virus in hospitalized patients with coronavirus disease—2019 (COVID19): duration and key determinants", medRxiv, Jun. 9, 2020, retrieved from the Internet: URL: https://www.medrixiv.org/content/10.1101/2020.06.08.20125310v1.full.pdf.

Wölfel R. et al., "Virological assessment of hospitalized patients with COVID-2019", Nautre, vol. 581, No. 7809, Apr. 1, 2020, pp. 465-469.

* cited by examiner

*Primary Examiner* — Barry A Chestnut

(74) *Attorney, Agent, or Firm* — Silvia Salvadori, P.C.; Silvia Salvadori

(57) ABSTRACT

Method for early determination of an active SARS-CoV2 infection, based on identification of subgenomic regions of the virus, and kits specifically designed for performing it.

13 Claims, 4 Drawing Sheets

Specification includes a Sequence Listing.

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 1

caaccaactt tcgatctctt gta                                               23


<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 2

tctgctccct tctgcgtaga                                                   20


<210> SEQ ID NO 3
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 3

acttcctcaa ggaacaacat tgcca                                             25


<210> SEQ ID NO 4
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 4

caaaccaacc aactttcgat ctcttgta                                          28
```

<210> SEQ ID NO 5
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 5
tctggttact gccagttgaa tc 22

<210> SEQ ID NO 6
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 6
cgatctcttg tagatctgtt ctc 23

<210> SEQ ID NO 7
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 7
atattgcagc agtacgcaca ca 22

<210> SEQ ID NO 8
<211> LENGTH: 26
<212> TYPE: DNA
<213> ORGANISM: Artificial Sequence
<220> FEATURE:
<223> OTHER INFORMATION: oligonucleotide probe

<400> SEQUENCE: 8
acactagcca tccttactgc gcttcg 26

<210> SEQ ID NO 9
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 9
caaaccaacc aactttcgat ctcttgta 28

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 10
agaagtacgc tattaactat t 21

<210> SEQ ID NO 11
<211> LENGTH: 19
<212> TYPE: DNA
<213> ORGANISM: Artificial Sequence
<220> FEATURE:
<223> OTHER INFORMATION: oligonucleotide primer

```
<400> SEQUENCE: 11

cacattggca cccgcaatc                                                    19


<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12

gaggaacgag aagaggcttg                                                   20


<210> SEQ ID NO 13
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 13

acttcctcaa ggaacaacat tgcca                                             25


<210> SEQ ID NO 14
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 14

gaccccaaaa tcagcgaaat                                                   20


<210> SEQ ID NO 15
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 15

tctggttact gccagttgaa tctg                                              24


<210> SEQ ID NO 16
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 16

cgatctcttg tagatctgtt ctc                                               23


<210> SEQ ID NO 17
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 17

tctggttact gccagttgaa tc                                                22


<210> SEQ ID NO 18
<211> LENGTH: 24
```

<212> TYPE: DNA
<213> ORGANISM: Artificial Sequence
<220> FEATURE:
<223> OTHER INFORMATION: oligonucleotide probe

<400> SEQUENCE: 18
tggaccccaa aatcagcgaa atgc 24

<210> SEQ ID NO 19
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 19
ccctgtgggt tttacactta a 21

<210> SEQ ID NO 20
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 20
acgattgtgc atcagctga 19

<210> SEQ ID NO 21
<211> LENGTH: 28
<212> TYPE: DNA
<213> ORGANISM: Artificial Sequence
<220> FEATURE:
<223> OTHER INFORMATION: oligonucleotide probe

<400> SEQUENCE: 21
ccgtctgcgg tatgtggaaa ggttatgg 28

<210> SEQ ID NO 22
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 22
acaggtacgt taatagttaa tagcgt 26

<210> SEQ ID NO 23
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 23
atattgcagc agtacgcaca ca 22

<210> SEQ ID NO 24
<211> LENGTH: 26
<212> TYPE: DNA
<213> ORGANISM: Artificial Sequence
<220> FEATURE:
<223> OTHER INFORMATION: oligonucleotide probe

<400> SEQUENCE: 24

-continued

```
acactagcca tccttactgc gcttcg                                        26


<210> SEQ ID NO 25
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 25

agatttggac ctgcgagcg                                                19


<210> SEQ ID NO 26
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 26

gagcggctgt ctccacaagt                                               20


<210> SEQ ID NO 27
<211> LENGTH: 23
<212> TYPE: DNA
<213> ORGANISM: Artificial Sequence
<220> FEATURE:
<223> OTHER INFORMATION: oligonucleotide probe

<400> SEQUENCE: 27

ttctgacctg aaggctctgc gcg                                           23


<210> SEQ ID NO 28
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 28

atgagcttag tcctgttg                                                 18


<210> SEQ ID NO 29
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 29

ctccctttgt tgtgttgt                                                 18


<210> SEQ ID NO 30
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 30

agatgtcttg tgctgccggt a                                             21
```

METHOD FOR DETERMINING ACTIVE SARS-CoV-2-INFECTIONS

Sequence listing named 1942PCT sequence list.txt, created on Jun. 9, 2023 and of size of 6127 bytes is incorporated herein by reference.

This application is a U.S. national stage of PCT/EP2021/087512 filed on 23 Dec. 2021, which claims priority to and the benefit of Italian Patent Application No. 102020000032351 filed on 23 Dec. 2020, the contents of which are incorporated herein by reference in their entireties.

The present invention relates to a method for early determination of an active SARS-CoV2 infection and for predicting the infection outcome in an individual, based on identification of the subgenomic RNAs of the virus, and a kit for implementing said method.

BACKGROUND OF THE INVENTION

Coronavirus SARS-CoV-2, the agent responsible for the disease COVID-19, has recently caused a pandemic with serious social and economic repercussions. In an endeavour to limit the effects of the pandemic, a great deal of effort has been expended on developing fast, reliable technologies designed to detect the virus at an early stage and reduce its spread.

One of the major challenges in the diagnosis of SARS-CoV-2 is associated with identification of asymptomatic carriers, who contribute significantly to the spread of the virus. Other difficulties are represented by early identification of the disease and the ability to detect only its symptoms, which are similar to, and therefore liable to be mistaken for, those of other respiratory disorders or influenza.

The SARS-CoV-2 detection techniques currently used can be divided into three groups: (i) molecular methods able to detect viral RNA sequences, (ii) rapid diagnostic tests that detect the host's viral antigens or antibodies, and (iii) imaging techniques that detect lung changes.

In the molecular approach, technologies based on PCR and high-throughput sequencing are commonly used to amplify nucleic acids and detect the presence of the virus in respiratory samples.

At present, the available diagnostic kits are based on detection of SARS-CoV-2 genes that encode both structural proteins (e.g. spike protein [S], envelope protein [E], membrane protein [M] and nucleocapsid protein [N]) and non-structural proteins (Orf1b/RdRp).

CoV viruses contain the largest genomes (26-32 kb) of all the RNA virus families. Each viral transcript has a 5'-cap protective structure and a 30 poly(A) tail (Lai and Stohlman, 1981; Yogo et al., 1977). On entry into the cell, the genomic RNA is translated to produce non-structural proteins (nsps) from two open reading frames (ORFs), ORF1a and ORF1b. The viral genome is also used as a replication and transcription template, mediated by nsp12 which harbours the activity of RNA-dependent RNA polymerase (RdRP) (Snijder et al., 2016; Sola et al., 2015). Negative-sense RNA intermediates are generated to serve as templates for positive-sense genomic RNA (gRNA) and subgenomic RNA (sgRNA) synthesis. All the structural and accessory proteins are translated by the sgRNAs of the CoVs. The gRNA is packed by the structural proteins to assemble progeny virions. Shorter subgenomic RNAs encode conserved structural proteins (spike protein [S], envelope protein [E], membrane protein [M] and nucleocapsid protein [N]), together with various accessory proteins. However, the ORFs have not yet been experimentally verified for expression. It is therefore not yet clear which accessory genes are actually expressed by this compact genome.

SARS-CoV-2 is known to have at least six accessory proteins (3a, 6, 7a, 7b, 8 and 10) according to the current annotation (GenBank: NC_045512.2). Taken together, SARS-CoV-2 expresses nine sgRNAs (S, 3a, E, M, 6, 7a, 7b, 8 and N) together with the gRNA (Cell. 2020; 181:914-921).

The functions of the sgRNAs are unclear, and some of them have been considered as parasites competing for viral proteins, hence their name of "defective interfering RNAs" (DI-RNA).

However, a certain association has been observed between the detection of sgRNAs and isolation of the virus in cell cultures, and in samples such as stool samples (J Infect 2020S0163-4453(20)30753-2). N sgRNA (sgN) is considered to be the transcript most abundantly expressed during viral replication, followed by E sgRNA (sgE); sgE is produced in amounts of transcript lower than about 1.5 Log 10 (J Infect 2020S0163-4453(20)30753-2).

Detection of more than one sgRNA could be used as a marker for viral replication, but further studies are required to confirm this hypothesis (Leung et al. Emerg Infect Dis 2020; 26:2701-4). It has also been suggested that detection of subgenomic RNA of SARS-CoV-2 in diagnostic samples is not a valid indicator of infection and replication of the virus [Alexandersen S et al. "SARS-CoV-2 genomic and subgenomic RNAs in diagnostic samples are not an indicator of active replication", *Nature Communications* volume 11, Article number: 6059 (2020)].

DESCRIPTION OF THE INVENTION

A method for early determination of the presence of SARS-Cov-2 infection, in the active stage and characterised by a high viral load, has now been found. The method according to the invention is based on detection of subgenomic RNA encoding nucleoprotein N (sgN) and subgenomic RNA encoding envelope protein (sgE), in a biological sample of the subject's cells or tissues, wherein positive detection of both subgenomic RNAs is indicative of an active infection state with high viral load.

The sample is generally taken from the subject's upper or lower respiratory tract with a nasal, oropharyngeal or nasopharyngeal swab. After collection, the sample is analysed for the presence of sgN and sgE using Real-Time PCR or Droplet Digital PCR (ddPCR). The subgenomic regions sgN and sgE can be detected together in the same RT-PCR or ddPCR reaction or in separate reactions starting with the same biological sample. The procedure comprises the following steps:

(1) extraction of RNA from sample;
(2) reverse transcription into cDNA
(3) amplification of cDNA using Real-Time PCR with TaqMan probes or using ddPCR.

Real-Time PCR technology is known in the art and combines the PCR technique with the use of fluorescent "reporter" molecules to monitor the formation of products of amplification during each cycle of the PCR reaction. Amplification of the target DNA is obtained by means of repeated denaturing cycles followed by pairing of the primers and probes and polymerase-catalysed primer extension. DNA amplification is monitored in each PCR cycle by measuring the fluorescent signal produced, for example by non-specific dyes intercalated in double-stranded DNA or by sequence-specific probes consisting of oligonucleotides labelled with a fluorescent reporter that allows detection after hybridisation with the complementary target DNA. Dyes suitable for intercalation include SYBR® (Green I, Green II, Gold), LCGreen®, SYTO-(9, 13, 16, 60, 62, 64, 82), BOBO-3, POPO-3, BEBO, TO-PRO3, PicoGreen®, SYTOX Orange and other commercially available fluorescent dyes (fluorophores). The oligonucleotide probe is labelled with a fluorescent reporter (fluorophore) at one end and a quencher at the opposite end of the probe. The 5' exonuclease activity of the polymerase cleaves the probe, releasing the reporter molecule, and resulting in increased intensity of fluorescence. Examples of fluorophores include 5- or 6-carboxyfluorescein (5- or 6-FAM), tetrachlorofluorescein (TET), hexachloro-6-carboxyfluorescein (HEX), 6-carboxy-4',5'-dichloro-2',7'-dimethoxyfluorescein succinimidyl ester (JOE), tetram ethyl rhodami ne (TAMRA), 5-carboxytetramethylrhodamine (TAMRASE), carboxy-X-rhodamine (ROX) and 4-(dimethylaminoazo)benzene-4-carboxylic acid (DABCYL). Examples of quenchers include those belonging to the BHQ (Black Hole Quencher) family, NFQ-MGB (non-fluorescent quencher and minor groove binder), and QSY 7 or 21 carboxylic acid succinimidyl ester.

Droplet Digital PCR (ddPCR) technology is a method for conducting digital PCR based on water-oil emulsion droplet technology. A sample is partitioned into 20,000 droplets, and PCR amplification of the template molecules takes place in each droplet. ddPCR technology uses reagents and workflows similar to those used for the majority of the standard tests based on TaqMan probes. The very large partitioning of the samples is a key aspect of the ddPCR technique.

In a preferred embodiment of the invention, the following are used to detect sgN with RT-PCR:

(a) the primer pair SEQ ID NO:1 and SEQ ID NO:2 and the probe SEQ ID NO:3, suitably labelled with a fluorophore-quencher pair;

or (b) the primer pair SEQ ID NO. 16 and SEQ ID NO:17 and the probe SEQ ID NO:18, suitably labelled with a fluorophore-quencher pair;

or (c) the primer pair SEQ ID NO:4 and SEQ ID NO:5 together with the SYBR®-Green dye.

The same primers and probes as identified in (a) and (b) are preferably used to detect sgN with ddPCR.

In another preferred embodiment, detection of sgE by RT-PCR is conducted with the primer pair SEQ ID NO:6 and SEQ ID NO:7 and the probe SEQ ID NO:8, suitably labelled with a fluorophore-quencher pair, or the primer pair SEQ ID NO:9 and SEQ ID NO:10 together with the SYBR-Green dye. The same primers, SEQ ID NO:6 and SEQ ID NO:7, and the labelled probe SEQ ID NO:8, are preferably used to detect sgE with ddPCR.

The RT-PCR reaction, wherein the indicated primers and probe are used, is preferably conducted in a thermocycler under the following conditions: (i) heating and denaturing at 50° C. for 2 min and 95° C. for 10 min; followed by (ii) PCR stage at 95° C. for 15 sec and 60° C. for 1 min, repeated for 60 cycles; followed by (iii) melt curve stage at 95° C. for 15 sec, 60° C. for 1 min and 95° C. for 15 sec.

The ddPCR reaction, wherein the indicated primers and probe are used, is preferably conducted in a thermocycler under the following conditions: (i) 95° C. for 10 min, followed by (ii) 95° C. for 30 sec and 55° C. for 1 min, repeated for 45 cycles, followed by (iii) 98° C. for 10 min.

In addition to the subgenomic RNAs for the genes of nucleoprotein N and envelope protein E, other genes or viral regions commonly used as target genes or sequences in commercial kits used to analyse nasal and/or oropharyngeal swab samples can also be detected. In particular, the target genes of the SARS-CoV2 virus are selected from gene E, gene N, RdRp, RNAse P and/or orf1ab. sgN, sgE and one or more of the other target genes can be detected simultaneously in a single RT-PCR reaction or by conducting a plurality of reactions in parallel or at different times, starting with the same biological sample.

The following sets of primers and probes are preferably used for detection of E and Orf1a genes (Arena F. et al., International Journal of Molecular Sciences 2021, 22, 1298, Table 2, pages 5 and 6):

Orf1ab:

```
Forward:
                                   (SEQ ID NO: 19)
CCCTGTGGGTTTTACACTTAA

Reverse:
                                   (SEQ ID NO: 20)
ACGATTGTGCATCAGCTGA

Probe:
                                   (SEQ ID NO: 21)
CCGTCTGCGGTATGTGGAAAGGTTATGG
```

Gene E:

```
Forward:
                                   (SEQ ID NO: 22)
ACAGGTACGTTAATAGTTAATAGCGT

Reverse:
                                   (SEQ ID NO: 23)
ATATTGCAGCAGTACGCACACA

Probe:
                                   (SEQ ID NO: 24)
ACACTAGCCATCCTTACTGCGCTTCG;
```

the following primers and probe are preferably used for detection of RNAse P gene (www.who.int/docs/default-source/coronaviruse/whoinhouseassays.pdf):

```
Forward:
                                   (SEQ ID NO: 25)
5'-AGATTTGGACCTGCGAGCG-3'

Reverse:
                                   (SEQ ID NO: 26)
5'-GAGCGGCTGTCTCCACAAGT-3'

Probe:
                                   (SEQ ID NO: 27)
5'FAM-TTCTGACCTGAAGGCTCTGCGCG-BHQ-1-3';
```

the following primers and probe are preferably used for detection of RdRp gene (www.who.int/docs/default-source/coronaviruse/whoinhouseassays.pdf):

```
Forward:
                                   (SEQ ID NO: 28)
ATGAGCTTAGTCCTGTTG

Reverse:
                                   (SEQ ID NO: 29)
CTCCCTTTGTTGTGTTGT

Probe:
                                   (SEQ ID NO: 30)
[5']Hex AGATGTCTTGTGCTGCCGGTA [3']BHQ-1;
```

and the following primers and probe are preferably used for detection of N gene:

```
Forward:
                                  (SEQ ID NO: 11)
CACATTGGCACCCGCAATC

Reverse:
                                  (SEQ ID NO: 12)
GAGGAACGAGAAGAGGCTTG

Probe:
                                  (SEQ ID NO: 13)
5'FAM- ACTTCCTCAAGGAACAACATTGCCA- BBQ-3'.
```

Detection of sgE serves as positive control for the analysis, and is indicative of SARS-CoV2 infection, even in the absence of sgN amplification. In particular, detection of sgE in the biological sample tested makes it possible to discriminate between SARS-CoV2 infection and infection with other SARS-CoV viruses (FluA, FluB, RSV, etc). Moreover, amplification of sgE in the absence of sgN indicates the presence of SARS-CoV-2 infection with a low viral load, whereas amplification of sgE together with sgN is indicative of infection with a high viral load.

Moreover, simultaneous amplification of a housekeeper gene such as beta globin can be performed as internal control of the reaction.

Various evaluations can therefore be made on the basis of the result of amplification of the subgenomic RNAs sgN and sgE in the test sample:

detection of both sgN and sgE indicates an early infection at the active stage with a high viral load; the subject may therefore be contagious;

detection of sgE but not sgN indicates that the subject is infected with SARS-CoV2, but possibly with a prior infection or late-stage infection; the subject may therefore not be contagious.

These evaluations are particularly useful in cases wherein the amplification of the target genes tested for by the kits currently on the market give results that are difficult to interpret or poorly indicative of the actual presence of infection, for example by showing positivity to only one of the different genome targets amplified.

The method according to the invention can therefore be conveniently applied to the screening of patients infected with the SARS-CoV2 virus, to identify patients at an active stage of infection, who are therefore potentially contagious.

In addition, it was found that sgN is the first transcript that becomes undetectable, compared with sgE transcript, during the recovery in both hospitalized and isolated COVID19-affected patients, indicating that sgN loss is a predictive marker for lower SARS-CoV2 replication activity, thus being of importance for both monitoring the therapeutic response and alerting clinicians that the SARS-CoV2 negativization process is underway.

Accordingly, in a further embodiment the invention provides a method for predicting viral negativization and consequent recovery from SARS-CoV2 infection in a patient, which comprises determining the levels of sgN and sgE RNAs in a biological sample from said patient at different times from the initial positive test for SARS-CoV2 infection, wherein a decreased expression of sgN over time or its lack of detection while the levels of sgE remain substantially unchanged, indicates benign SARS-CoV-2 negativization in said patient.

Detection of sgN over time can be carried out with the methods and reagents herein disclosed, particularly using RT-PCR.

In a preferred embodiment, the patient is analysed for sgN expression at 3 to 7 days intervals from the test indicating SARS-CoV2 positivity.

Overall, the experimental results show that SgN is a biomarker that is predictive of virus replication loss in patients infected with SARSCoV-2. This enables reducing the risk of further infection considering those under an active viral load versus those who are in remission in terms of disease transmission and virus infectivity. Furthermore, sgN detection can be used during the follow-up of hospitalized and home-isolated COVID19-positive patients, to monitor their disease progression and therapeutic responses.

A further aspect of the invention relates to a kit for implementing the methods described herein. The kit comprises the primers and probes disclosed in Table 1 for detection of sgN and/or sgE RNAs in a biological sample and optionally the primers and probes herein diclosed for detecting other gene transcripts from E, N, RdRp, RNAse P and/or Orf1ab genes.

EXPERIMENTAL SECTION

Sample Collection

Figure 1:
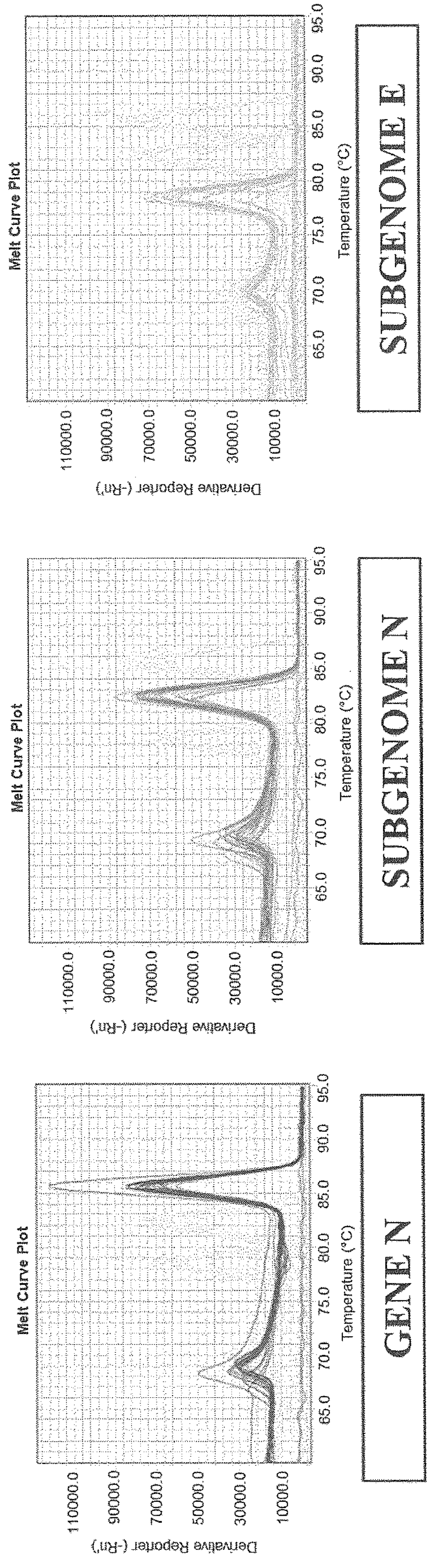
FIG. 1: Melt profiles obtained by HRMA on the different genomic and subgenomic regions of SARS-Cov_2. The amplification plots clearly show that the three melting temperatures (Tm) are different: Gene N (Tm=86.5), sgN (Tm=82.5) and sgE (78.0) respectively.

The naso-oropharyngeal swab samples were taken with commercial flocked swabs collected in about 1 mL of universal transport medium (UTM; Copan, Brescia, Italy) and sent to our laboratory in containers at a controlled temperature within four hours of the sample being taken. A unique centralised unit for sample collection, consisting of qualified healthcare professionals trained to take oropharyngeal swabs, guaranteed the homogeneity of the sample-taking procedures. Our study was approved by the Ethics Committee of Federico II University (protocol no. 000576 of Oct. 4, 2020) and conducted in compliance with the Declaration of Helsinki.

RNA Extraction

All samples were extracted by an automated procedure on MagPurix instrumentation. In detail, a 200 μL volume was used to extract RNA in a fully automated system based on MAGPURIX VIRAL/PATHOGEN NUCLEIC ACIDS kit (Zinexts, marketed by Resnova, Italy) running on the MAGPURIX 24 instrument. MagPurix® CE-IVD reagent kits are designed to provide the maximum extraction quality, through optimised protocols. All the RNA was eluted in 50 μl of elution buffer supplied by the manufacturers.

Amplification of Orf1ab, N and E Regions Amplification

The oligonucleotide sequence of the primers is described in Table 1. Total RNA was extracted from all positive samples. The sgRNA RT-PCR assay used the SuperScript IV VILO Master Mix (11756500, Invitrogen) according to the manufacturer's instructions. The sgRNA tests used a leader-specific primer, as well as primers and probes targeting sequences downstream of the start codons of genes E and N [10, 11]. In addition, SYBR-green technology was also used to detect said subgenomic transcripts with a different couple of primers. In detail, the reverse transcription products (cDNA) were amplified by quantitative PCR in real time, using a real-time PCR system (Quantstudio 5). The target genes were detected with a Brightgreen 2× qPCR Mastermix low-rox (#Mastermix-lr; ABM.). These analyses were conducted with a PCR machine (Quantstudio 5) under the following conditions: Heating/denaturing step, 50° C. for 2 min, 95° C. for 10 min; PCR stage, 95° C. for 15 sec, 60° C. for 1 min (×60 cycles); Melt curve stage, 95° C. for 15 sec, 60° C. for 1 min; 95° C. for 15 sec. The SYBER primers are reported in Table 1.

TABLE 1

Primers used for both real-time PCR and ddPCR

| Viral target gene | Primers | Sequence of Primers |
|---|---|---|
| Sg-N[7, 13] (TaqMan) | Forward | CAACCAACTTTCGATCTCTTGTA (SEQ ID NO: 1) |
| | Reverse | TCTGCTCCCTTCTGCGTAGA (SEQ ID NO: 2) |
| | Probe | 5'FAM-ACTTCCTCAAGGAACAACAT-TGCCA-BBQ-3' (SEQ ID NO: 3) |
| Sg-N (TaqMan) | Forward | CGATCTCTTGTAGATCTGTTCTC (SEQ ID NO: 16) |
| | Reverse | TCTGGTTACTGCCAGTTGAATC (SEQ ID NO: 17) |
| | Probe | 5'-FAM-TGGACCC-CAAAATCAGCGAAATGC-BBQH1-3' (SEQ ID NO: 18) |
| SYBR-Green | Forward | CAAACCAACCAACTTTCGATCTCTTGTA (SEQ ID NO: 4) |
| | Reverse | TCTGGTTACTGCCAGTTGAATC (SEQ ID NO: 5) |
| Sg-E[12] (TaqMan) | Forward | CGATCTCTTGTAGATCTGTTCTC (SEQ ID NO: 6) |
| | Reverse | ATATTGCAGCAGTACGCACACA (SEQ ID NO: 7) |
| | Probe | 5'FAM-ACACTAGCCATCCT-TACTGCGCTTCG-BBQ-3' (SEQ ID NO: 8) |
| SYBR-Green | Forward | CAAACCAACCAACTTTCGATCTCTTGTA (SEQ ID NO: 9) |
| | Reverse | AGAAGTACGCTATTAACTATT (SEQ ID NO: 10) |
| N_gene[7] (TaqMan) | Forward | CACATTGGCACCCGCAATC (SEQ ID NO: 11) |
| | Reverse | GAGGAACGAGAAGAGGCTTG (SEQ ID NO: 12) |
| | Probe | 5'FAM-ACTTCCTCAAGGAACAACAT-TGCCA-BBQ-3' (SEQ ID NO: 13) |

TABLE 1-continued

Primers used for both real-time PCR and ddPCR

| Viral target gene | Primers | Sequence of Primers |
|---|---|---|
| SYBR-Green | Forward | GACCCCAAAATCAGCGAAAT (SEQ ID NO: 14) |
| | Reverse | TCTGGTTACTGCCAGTTGAATCTG (SEQ ID NO: 15) |

Digital Droplet PCR (ddPCR)

The absolute quantification of SARS-CoV2-RNA was carried out by ddPCR using a two-step reaction: cDNA was synthesized with the SensiFAST cDNA Synthesis Kit (Bioline), using 2× ddPCR Supermix (no dUTP) (Bio-Rad). The QX200 droplet generator was used to generate the droplets by mixing the cDNA samples, 9 μM of forward and reverse primers, and 2.5 μM of probe with 70 μL of droplet formation oil. The amplification step was performed on the T100 thermocycler (Bio-Rad) under the following conditions: heating at 95° C. for 10 minutes, followed by 95° C. for 30 seconds and 55° C. for 1 minute, repeated for a total of 45 cycles (at a heating rate of 2° C./s), followed by 98° C. for 10 minutes. After PCR, the positive/negative droplets were analysed in the QX200 droplet reader (Bio-Rad), and QuantaSoft analysis software (Bio-Rad) was used to calculate the number of targets analysed.

Statistical Analysis

The statistical analyses were conducted with the IBM SPSS® Statistics software package (IBM Company, New York, N.Y., USA) (IBM SPSS Statistics for Mac, version 26). The correlation matrix (Spearman's rho coefficient) was used to show the linear relationship between the diagnostic tests. P≤0.05 was considered statistically significant.

Results

We analysed 48 RNA samples extracted from patients who tested positive for COVID19 with Ct values ranging from 13.5-22.5 (no.=26) to >22.5-40 (no.=22). The target sgN was only detectable in the samples with Ct values close to or lower than 22.5. Conversely, sgE was always detected independently in the Ct value range. These results were obtained with both real-time TaqMan technology and SYBR Green. Moreover, by means of high-resolution melting analysis (HRMA), it was possible to distinguish between the different targets amplified, excluding the false positives which could have been generated by off-target signals (FIG. 1). Finally, we re-analysed said samples by droplet digital real-time PCR (ddPCR) to evaluate whether the absence of sgN in samples above Ct 22.5 was due to the detection limit of the Real-time method or rather to the characteristics of samples containing a lower viral load.

Figure 2:
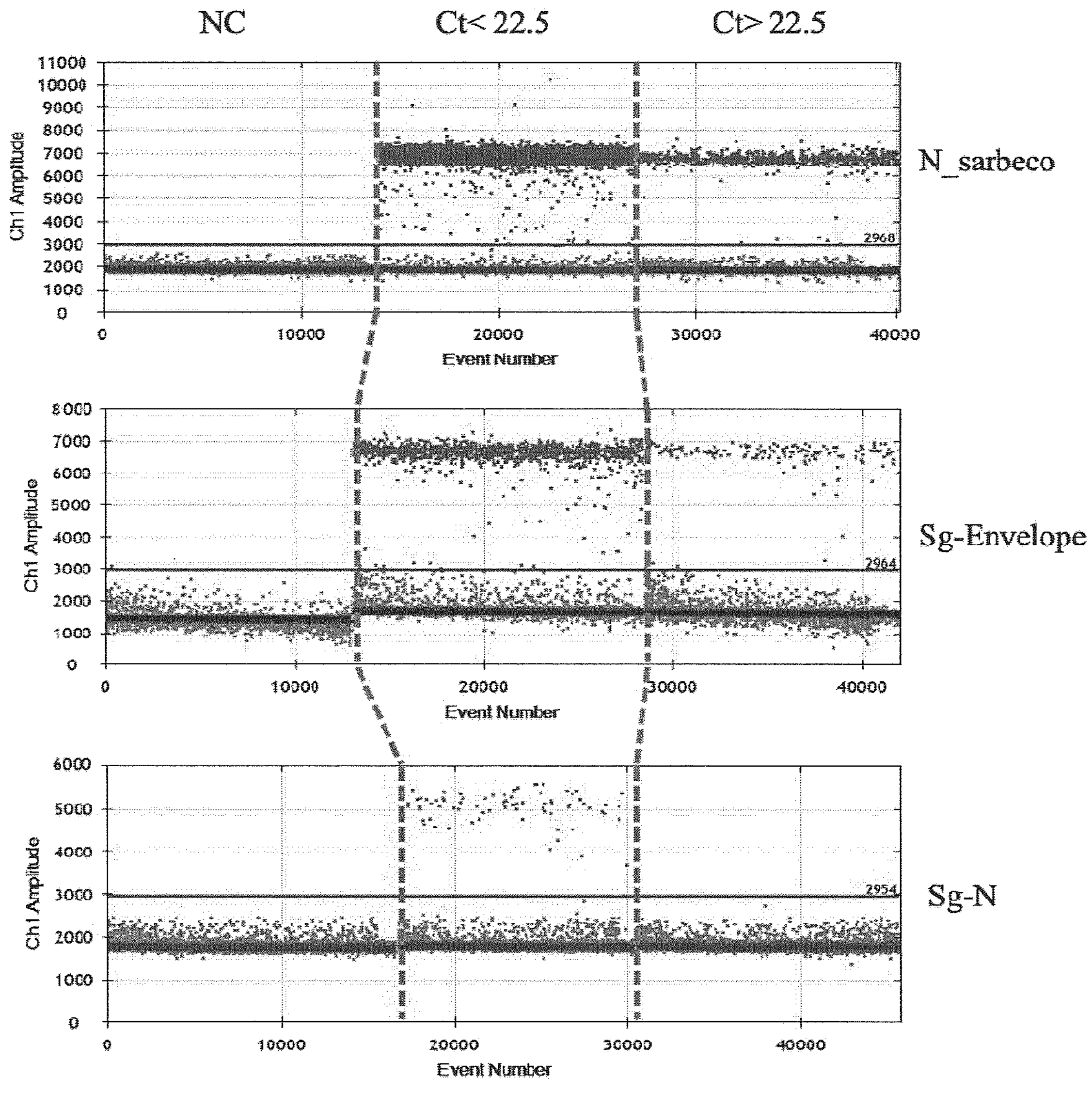
FIG. 2: ddPCR analysis of samples with low Ct (≤22.5) for transcripts of N, sgE and sgN FIG. 3. SgN and sgE are detected in samples from COVID19-affected patients with high SARS-CoV-2 viral load.

Our ddPCR results (FIG. 2) clearly show that sgE is detected in samples with Ct> or ≤22.5 (from 13.5 to 40), whereas the sgN is only detected when Ct is ≤22.5. It is interesting that sgN expression does not appear to be influenced by genomic N gene transcription, as N gene is detectable in the overall Ct range (from 13.5 to 40.0). These observations indicate that a) sgN is a marker for an early viral phase with a high load, b) the presence of sgE confirms that the positivity of the samples is due to SARS-CoV-2 infection, not to another SARS-CoV virus. sgE and sgN are therefore two specific markers for SARS-COV-2 infection.

SgN and sgE are Detected in Samples from COVID19-Affected Patients with High SARS-CoV-2 Viral Load We have developed a diagnostic kit based on a Taqman approach, that can detect expression levels of viral sgN, gene E, gene ORF1ab, and the human RNAse P gene. We compared the results obtained from 50 oro/nasopharyngeal swabs to those obtained using the "in-vitro diagnostic" (IVD) approved Allplex 2019-nCoV assay (Seegene; www.seegene.com/).

The SARS-CoV-2 kit also identified viral sgN, gene E, and gene ORF1ab in SARS-CoV-2-positive bronchial aspirate specimens collected from hospitalized patients.

The SARS-CoV-2 kit was also evaluated for sensitivity (sgN, gene E, gene ORF1ab; 300,000 to 30 viral copies) and for sgN specificity (≥99.9%), with a hit rate of 95.0%. We tested the detection of SARS-CoV-2 sgN transcripts using the SARS-CoV-2 kit through the analysis of oro/nasopharyngeal swab samples from a cohort of 315 COVID19-positive Italian patients (in Coronet Laboratories based in Milan, Udine, Naples). The positivity of these patients to SARS-CoV-2 infection was confirmed through detection of viral gene E and gene ORF1ab in all of the samples. In contrast, the levels of sgN were not detectable (i.e., Ct>40) in 120 of these samples (38.1%). One-way analysis of variance (ANOVA) was used to determine that sgN expression was detected using the SARS-CoV-2 kit only in the samples that were characterized by Ct values<33.163 for viral gene E (P<0.0001; FIG. 3A) and <33.155 for gene ORF1ab (P<0.0001; FIG. 3B). Furthermore, as expected, the expression levels of the human RNAse P gene did not influence the detection of viral sgN. Altogether, these data confirm that expression of viral sgN was detected using the SARS-CoV-2 kit only in those samples with higher viral loads, in a large cohort analysis.

We also compared sgE expression levels (using Taqman methodology) to sgN expression levels in 122 patients from one of the single Coronet centers, as part of the full cohort (ASL Napoli3-sud; Data S4). These data showed that sgN and sgE were not detectable using the SARS-CoV-2 kit in terms of their levels of expression in 82.8% and 64.8% of this single-center cohort, respectively (FIG. 3C, D). ANOVA was again used to determine that sgN expression was detected using the SARS-CoV-2 kit only in those patients with Ct values <33.4 for viral gene E (P<0.0001; FIG. 3E) (gene E cut-off as the limit of detection) and <33.54 for gene ORF1ab (P<0.0001; FIG. 1G) (gene ORF1ab cut-off for the limit of detection). These analyses showed similar results also for the entire cohort (i.e., 315 samples; FIG. 3A, B). For the expression of sgE levels, detection was seen using the SARS-CoV-2 kit when the Ct values for viral gene E and gene ORF1ab were <34.06 and <34.20, respectively (P<0.001, for both; FIG. 3F, H).

Taken together, these data indicated that both of the sgRNA transcripts (i.e., sgN, sgE) are independently detected only in those patients with higher viral loads, when the infection is expanding and rapidly progressing. Vice-versa, at lower viral loads, sgN was generally not detected (gene E Ct>33.16; gene Orf1b Ct>33.15; see FIG. 3A-B). Similarly, considering the lower viral loads, the expression of sgE was not detectable (gene E Ct>34.06; gene ORF1ab Ct>34.2; see FIG. 3F, H).

Figure 3:
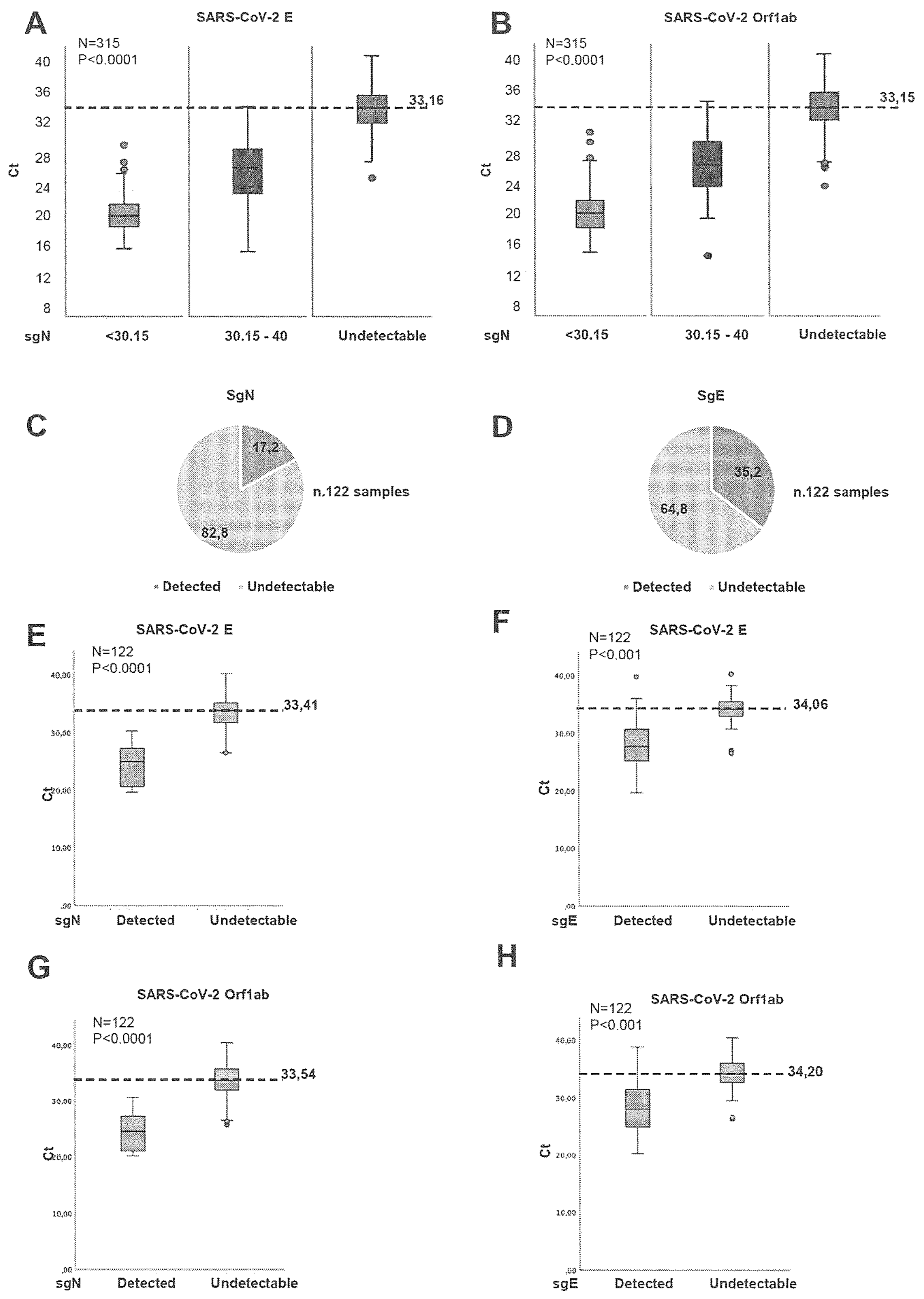

Detailed Description of FIG. 3

(A,B). Samples obtained from oro/nasopharyngeal swabs from COVID19-positive patients (N=315) were stratified into three groups according to the median Ct values of sgN (sgN Ct median=33.51), as detected through SARS-CoV-2 kit. The first group consisted of those samples where Ct for sgN was below the median value (i.e., Ct<30.51; n=99 samples; light grey). The second group was characterized by Ct values for sgN from the Ct median value (30.51) to 40.00 (n=96 samples; dark grey). The third group comprised samples where sgN was not detected (i.e., Ct>40; n=120 samples; grey). ANOVA was used through IBM SPSS Statistics to determine the cut-off for sgN detection. SgN was detected in the samples with viral E Ct values <33.163 (A) and ORF1ab Ct values <33.155 (B) (P<0.0001, for both). (C, D) Pie charts showing the proportions (%) of the oro/nasopharyngeal swab specimens where the levels of sgN (C) and sgE (D) were detectable (i.e., Ct values<40; dark grey) or not detectable (i.e., Ct values>40; grey), for the 122 COVID19-positive patients belonging to a single cohort (entire cohort, N=315). The data show no detectable levels of sgN and sgE in 82.8% (C; grey) and 64.8% (D; grey) of the patients, respectively. (E-H) ANOVA was used through IBM SPSS Statistics to determine the cut-off for sgN and sgE detection in the 122 oro/nasopharyngeal swabs from the single-cohort COVID19-positive patients. SgN was detected in the samples with viral E Ct values<33.41 (E) and ORF1ab Ct values<33.54 (G) (P<0.0001, for both). SgE was detected in the samples with viral E Ct values<34.06 (E) and ORF1ab Ct values<34.20 (G) (P<0.001, for both).

Loss of Detection of sgN Precedes SARS-CoV-2 Replication Failure in Home-Isolated and Hospitalized COVID19-Affected Patients With the aim to monitor viral replication and its potential failure, we undertook further analyses to answer the question of how the longitudinal expression occurs for the sgRNAs (i.e., sgN, sgE) and for the genes N, E, ORF1ab and RpRd that are expressed during SARS-CoV-2 infection. Here, we analyzed a cohort of oro/nasopharyngeal swabs collected from 16 COVID19-positive home-isolated patients at specific times (i.e., 3-day intervals from the first swab) until they reached a negative status for the SARS-CoV-2 genes, when possible (FIG. 4A). Among these 16 patients, 10 were followed up to 7 days from the first swab analysis, and the remaining 6 patients to 6 days (FIG. 4A). We used both kits (i.e., SARS-CoV-2 kit, and Allplex 2019-nCoV assay) with these oro/nasopharyngeal swabs to determine the levels of viral sgN, gene E, gene ORF1ab, gene N and human RNase P gene. Three days and 7 days from the first swab, sgN was detected in 44% and 10%, respectively, of the patients (FIG. 4B). In contrast, loss of detection of the other viral genes was seen for patients 7 days from the first swab test (detected in: gene E, 20%; gene ORF1ab, 20%; gene N, 30%; RdRp 10%) (FIG. 4B). In the same cohort analysis, sgE was detected in 100% of the patients after 3 days, and in only 13% after 7 days (FIG. 4B) while the other genes analyzed here were detected at the same levels as discussed above.

In more detail, gene ORF1ab and RdRp were detected only in 10% of the patients 7 days from the first swab (FIG. 4B). Similarly, genes E and N were detected in 20% and 30%, respectively, of the patients 7 days from the first swab (FIG. 2B). This thus indicated that the loss of detection of sgN, and not sgE, was predictive of viral negativization after SARS-CoV-2 infection.

We then analyzed an independent cohort of six COVID19-affected patients hospitalized in an Intensive Care Unit. Here, the analysis monitored sgN, gene E, gene ORF1ab, gene N, and RdRp using longitudinal detection at 7-day intervals (0, 7, 14 days). SgN was detected on the first swab tests, and again in 67% of the patients after 7 days, and in 33% after 14 days (FIG. 4C, D). Then there was loss of detection of the other viral genes in these patients after 7 days and 14 days (detected in, respectively: gene E, 83%, 50%; gene ORF1ab, 83%, 50%; gene N, 67%, 50%; RdRp, 67%, 50%).

Taken together, these data obtained through the analysis of two independent datasets of oro-pharyngeal swab tests from COVID19-affected patients (home-isolated, hospitalized) identified sgN as the first viral transcript to show decreased expression levels (to the ‘undetectable’ level) during their recovery period of SARS-CoV-2 infection. Overall, sgN detection preceded the benign SARS-CoV-2 negativization by 3 to 7 days from the first swab in home-isolated and hospitalized COVID19-positive patients, respectively.

Figure 4:
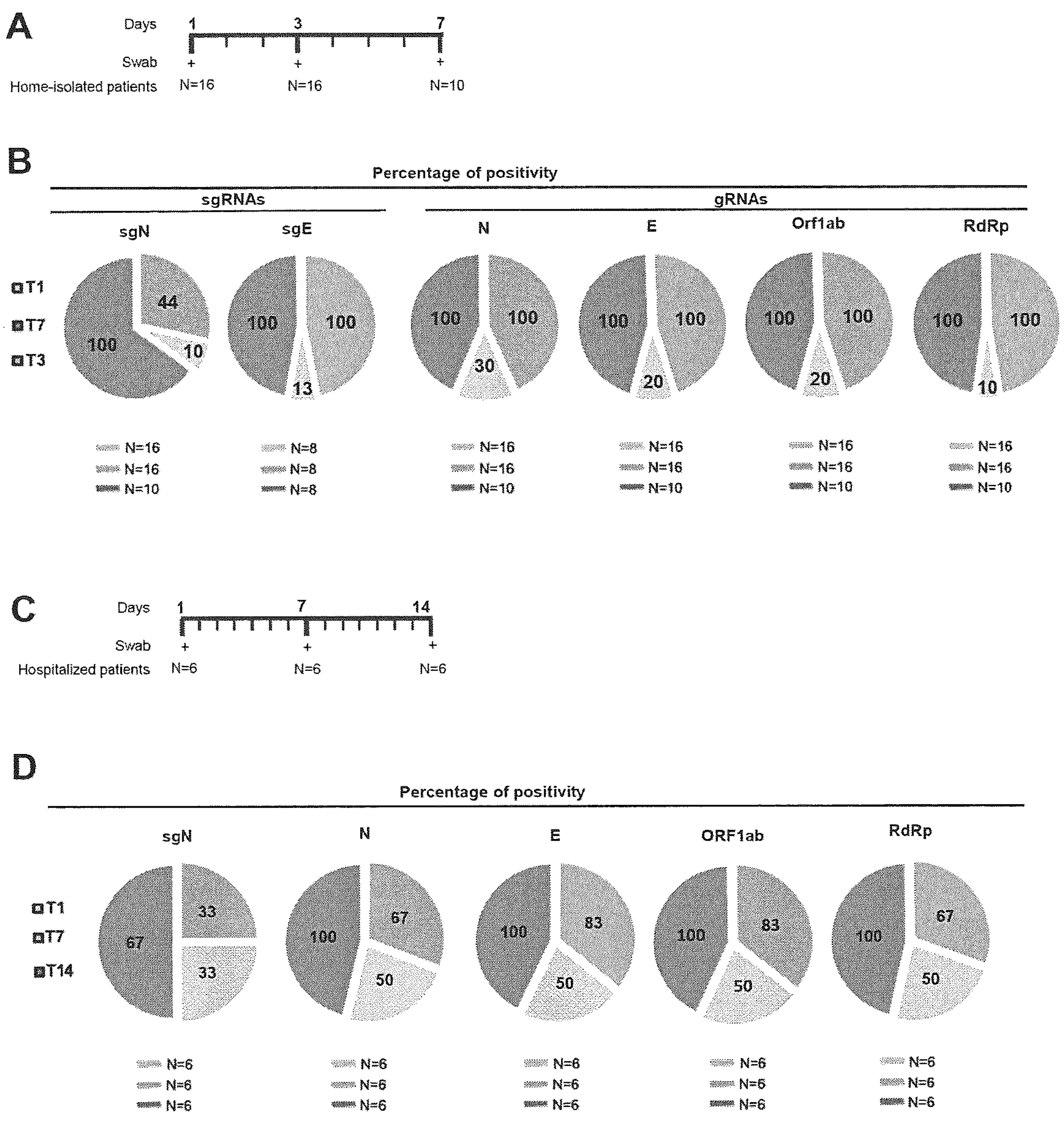
FIG. 4. Loss of detection of sgN precedes SARS-CoV-2 replication failure in home-isolated and hospitalized COVID19-affected patients.

Detailed Description of FIG. 4

(A) A cohort of oro/nasopharyngeal swabs was collected from home-isolated COVID19-positive patients and analyzed according to the scheduled times (i.e., at 3-days intervals from the first swab). Ten patients were followed up to 7 days from the first swab test; 6 patients were followed up to 3 days. (B) Pie charts showing the proportions (%) of positivity of the oro/nasopharyngeal samples to viral subgenomic sgN and sgE, and genomic N, E, ORF1ab, and RdRp at the different times (dark grey, first swab [n=16]; grey, second swab collected after 3 days [n=16]; light grey, third swab collected after 7 days [n=10]). SgE was detected in 8 oro/nasopharyngeal samples. SgN was detected in 44% of the samples after 3 days from the first swab. sgN, gene E and gene ORF1ab were measured using the SARS-CoV-2 kit. Gene N, gene E and gene ORF1ab were detected using the Allplex 2019-nCoV assay. SgE was evaluated by Taqman qPCR. (C) A cohort of oro/nasopharyngeal swabs collected from 6 hospitalized COVID19-positive patients was analyzed according to the scheduled times (i.e., 7-days intervals from the first swab). (D) Pie charts showing the proportions (%) of positivity of the oro/nasopharyngeal samples to viral subgenomic sgN, and genomic N, E, ORF1ab and RdRp at the different time points (dark grey, first swab [n=4]; grey, second swab collected after 7 days [n=4]; light grey, third swabs collected after 14 days [n=4]). SgN was detected in 50% of the samples after 7 days from the first swab. sgN, gene E and gene ORF1ab were measured using the SARS-CoV-2 kit. N and ORF1ab were detected using the Allplex 2019-nCoV assay.

The invention claimed is:

1. An in vitro method for determining the presence of active SARS-CoV2 infection in a subject, wherein said infection is at an early stage and is characterised by a high viral load, said method comprising detecting viral subgenomic RNA encoding the nucleoprotein N (sgN) and viral subgenomic RNA encoding the envelope protein (sgE) in a biological cell or tissue sample from the subject.

2. The method according to claim 1, wherein said biological cell or tissue sample is taken from the subject's upper or lower respiratory tract and is collected from a nasal, oropharyngeal or nasopharyngeal swab.

3. The method according to claim 1, wherein the detection of sgN and sgE RNAs is carried out by Real-Time PCR or Droplet Digital PCR (ddPCR) on corresponding cDNAs.

4. The method according to claim 3, wherein:

(a) sgN is detected by RT-PCR using:

(i) the primer pair SEQ ID NO:1 and SEQ ID NO:2 and the probe SEQ ID NO:3 labelled with a fluorophore-quencher pair;

or (ii) the primer pair SEQ ID NO:16 and SEQ ID NO:17 and the probe SEQ ID NO: 18 labelled with a fluorophore-quencher pair;

(iii) the primer pair SEQ ID NO:4 and SEQ ID NO:5 and SYBR-Green dye;

(b) sgE is detected by RT-PCR using:

(iv) the primer pair SEQ ID NO:6 and SEQ ID NO:7 and the probe SEQ ID NO: 8 labelled with a fluorophore-quencher pair;

or (v) the primer pair SEQ ID NO:9 and SEQ ID NO:10 and SYBR-Green dye;

(c) sgN is detected by ddPCR using:

(vi) the primer pair SEQ ID NO:1 and SEQ ID NO:2 and the probe SEQ ID NO: 3 labelled with a fluorophore-quencher pair;

(vii) the primer pair SEQ ID NO:16 and SEQ ID NO:17 and the probe SEQ ID NO: 18 labelled with a fluorophore-quencher pair;

(d) sgE is detected by ddPCR using the primer pair SEQ ID NO:6 and SEQ ID NO: 7 and the probe SEQ ID NO:8 labelled with a fluorophore-quencher pair.

5. The method according to claim 4, wherein:

(a) the RT-PCR is run in a thermocycler applying the following conditions: (i) 50° C. for 2 min, 95° C. for 10 min; followed by (ii) 95° C. for 15 sec, 60° C. for 1 min, repeated for 60 cycles; followed by (iii) 95° C. for 15 sec, 60° C. for 1 min, 95° C. for 15 sec;

(b) the ddPCR is run in a thermocycler applying the following conditions: (i) 95° C. for 10 min, followed by (ii) 95° C. for 30 sec and 55° C. for 1 min, repeated for 45 cycles; followed by (iii) 98° C. for 10 min.

6. The method according to claim 1, further comprising detecting one or more transcripts of the following viral genes in the biological sample: E, N, RdRp, RNAse and/or Orf1ab genes.

7. The method according to claim 1, for screening subjects infected by SARS-CoV2 virus.

8. An in vitro method for predicting viral negativization after SARS-CoV2 infection in a patient, said method comprising determining the levels of sgN and sgE RNAs in a biological sample from said patient at different times from SARS-CoV2 infection detection, wherein a decreased expression of sgN over time or the loss of sgN detection while the sgE detection levels remain unchanged, indicates benign SARS-CoV-2 negativization in said patient.

9. The method of claim 8, wherein said sgN RNA levels are detected by RT-PCR using (i) primer pair SEQ ID NO:1 and SEQ ID NO:2 and probe SEQ ID NO:3 labelled with a fluorophore-quencher pair;

or (ii) primer pair SEQ ID NO:16 and SEQ ID NO:17 and probe SEQ ID NO:18 labelled with a fluorophore-quencher pair;

(iii) primer pair SEQ ID NO:4 and SEQ ID NO:5 and SYBR-Green dye.

10. The method of claim 8, wherein the patient is analysed for sgN expression at 3 to 7 days intervals from SARS-CoV2 infection detection.

11. The method of claim 10, wherein said SARS-CoV2 infection is detected by analysis of a nasal, oropharyngeal or nasopharyngeal swab.

12. A kit for performing the method according to claim 1, which comprises primers and probes for detecting sgN and/or sgE RNAs in a biological sample, and optionally primers and probes for detecting one or more of E, N, RNAse, RdRp and/or Orf1ab gene transcripts, wherein (a) sgN is detected by RT-PCR using:

(i) primer pair SEQ ID NO:1 and SEQ ID NO:2 and probe SEQ ID NO:3 labelled with a fluorophore-quencher pair;

or (ii) primer pair SEQ ID NO:16 and SEQ ID NO:17 and probe SEQ ID NO:18 labelled with a fluorophore-quencher pair;

(iii) primer pair SEQ ID NO:4 and SEQ ID NO:5 and SYBR-Green dye;

(b) sgE is detected by RT-PCR using:

(iv) primer pair SEQ ID NO:6 and SEQ ID NO:7 and probe SEQ ID NO:8 labelled with a fluorophore-quencher pair;

or (v) primer pair SEQ ID NO:9 and SEQ ID NO:10 and SYBR-Green dye;

(c) sgN is detected by ddPCR using:

(vi) the primer pair SEQ ID NO:1 and SEQ ID NO:2 and the probe SEQ ID NO: 3 labelled with a fluorophore-quencher pair; or (vii) the primer pair SEQ ID NO:16 and SEQ ID NO:17 and the probe SEQ ID NO: 18 labelled with a fluorophore-quencher pair;

(d) sgE is detected by ddPCR using the primer pair SEQ ID NO:6 and SEQ ID NO: 7 and the probe SEQ ID NO:8 labelled with a fluorophore-quencher pair.

13. The kit of claim 12, wherein said primers and probes used for detecting E, N, RdRp, RNAse P and Orf1ab gene transcripts are the following:

E: primers SEQ ID NOs: 22,23; probe SEQ ID NO:24

N: primers SEQ ID NOs: 11,12; probe SEQ ID NO:13

RdRp: primers SEQ ID NOs: 28,29; probe SEQ ID NO:30

RNAse P: primers SEQ ID NOs: 25,26; probe SEQ ID NO:27

Orf1ab: primers SEQ IOD NOs: 19, 20; probe SEQ ID NO:21.

* * * * *